United States Patent [19]

Gritzner

[11] 4,043,895
[45] Aug. 23, 1977

[54] ELECTROPHORESIS APPARATUS

[75] Inventor: Gerhard Gritzner, Midland, Mich.

[73] Assignee: The Dow Chemical Company, Midland, Mich.

[21] Appl. No.: 662,499

[22] Filed: Mar. 1, 1976

Related U.S. Application Data

[62] Division of Ser. No. 360,990, May 16, 1973, Pat. No. 3,989,613.

[51] Int. Cl.² .................................... B01D 13/02
[52] U.S. Cl. .................. 204/301; 204/180 R; 204/180 P
[58] Field of Search ............... 204/151, 180 P, 301

[56] References Cited

U.S. PATENT DOCUMENTS

| | | | |
|---|---|---|---|
| 3,165,460 | 1/1965 | Zang et al. | 204/301 |
| 3,214,362 | 10/1965 | Juda | 204/151 X |
| 3,582,488 | 6/1971 | Zeineh | 204/180 R |
| 3,617,545 | 11/1971 | Dubois et al. | 204/180 P X |
| 3,649,511 | 3/1972 | Danly et al. | 204/252 |
| 3,677,923 | 7/1972 | Bier | 204/180 P |

Primary Examiner—Arthur C. Prescott
Attorney, Agent, or Firm—J. M. Kuszaj

[57] ABSTRACT

A continuous balanced flow electrophoresis apparatus utilizes a fixed, colloid-permeable boundary membrane across which net liquid flow is minimized. The apparatus is employed in electrophoretic separation of colloids such as blood plasma proteins in which fluid flow rates are controlled and balanced to minimize or prevent liquid transfer across the boundary membrane.

5 Claims, 3 Drawing Figures

ELECTROPHORESIS APPARATUS

CROSS-REFERENCE TO RELATED APPLICATION

This is a division, of application Ser. No. 360,990 filed May 16, 1973, now U.S. Pat. No. 3,989,613.

BACKGROUND OF THE INVENTION

The present invention is concerned with an apparatus for the separation of suspensions and solutions by means of electrophoresis. Various types of electrophoretic separations are known, including continuous free-boundary electrophoresis, exemplified by Bier, U.S. Pat. No. 2,878,178; electrodecantation, exemplified by Polson, U.S. Pat. No. 2,801,962; and forced flow electrophoresis, exemplified by Bier, U.S. Pat. No. 3,079,318.

Separations utilizing electrophoretic migration of an electrically charged colloidal component through a colloid permeable membrane are known and can be carried out on known apparatus after modification in accordance with the invention. Such apparatus typically comprises a compartment defined by a pair of semipermeable membranes which separate the compartment from a pair of electrodes, and at least one colloid permeable boundary membrane which divides the compartment into at least one pair of cells. Many apparatus will include a stack of cell pairs, each pair being separated by a semipermeable membrane. Appropriate fluid inlets and outlets, and appropriate electrical circuitry are provided to pass fluids through the cell pairs and to apply a direct current electric field across the permeable membrane. Apparatus of this general type is described, for example, by Milan Bier, U.S. Pat. No. 3,079,318. Such apparatus utilizes forced flow electrophoresis, in which the colloid permeable membrane serves as a filter through which liquid is forced by adjustment of pressure and flow rates through the cells. Such separations have been described by Smolka and Logan, Preparative Biochemistry, 2 (4), 329–45 (1972).

BRIEF SUMMARY OF THE INVENTION

This invention is directed to an improved electrophoretic apparatus. More particularly, the invention is directed to a fixed boundary continuous electrophoretic apparatus useful for continuous separation of colloidal suspensions and solutions. The apparatus comprising a compartment defined by semipermeable, non-conducting membranes, a colloid permeable membrane in the compartment dividing the compartment into a pair of cells, electrodes for applying a direct current electric field across the boundary, a fluid inlet and outlet communicating with opposite ends of the cell in each pair of cells, means for introducing fluid into each cell, passing fluid along the surface of the colloid permeable membrane and withdrawing fluid from the cell, and means for balancing the fluid flow on opposite sides of the boundary membrane to minimize or eliminate net fluid transport through the colloid permeable boundary membrane.

In the practice of the present invention a colloidal solution is introduced into one end of an electrophoresis cell and passed along one face of a colloid permeable non-conducting boundary membrane and withdrawn from the other end of the cell at a volumetric rate of approximately equal to its rate of introduction; a second solution is passed along the opposite surface of the boundary membrane in a corresponding manner while a direct current electric field is applied across the membrane and the two solutions, thereby inducing electrophoretic migration of an electrically charged component of one of the solutions across the boundary, thereby increasing the concentration of said component in the liquid on the other side of said boundary. At the same time, electrically neutral components and components of opposite charge (to the migrating components) are retained on their original side of the boundary.

The invention can utilize many elements of the cell stack apparatus similar to those utilized in forced flow electrophoresis or electrofiltration, however, in the present apparatus net liquid flow through the colloid permeable boundary element is virtually eliminated. However, many of the known general parameters of electrophoretic separations are applicable to the invention, and can be dealt with in ways analogous to known methods. For example, there may be mentioned 1. General relationship of electrophoretic mobility, migration velocity of the charged species and polarity and strength of the electric field;
2. Generation of heat by the electric current and cooling of the colloidal liquid being treated;
3. Migration of non-colloidal electrolytes through the boundary and balancing of electrolyte content on opposite sides of the boundary;
4. Spatial configuration of the apparatus for gravitational stability;
5. Generation of gases at the electrodes, and venting of the apparatus;
6. Use of non-conducting materials for the membranes, boundary diaphragm, enclosure, etc. Such considerations are well known, and are discussed in the prior art (e.g. Bier U.S. Pat. No. 3,079,318) and need not be described in detail here.

In balanced flow electrophoresis using the present apparatus it is essential that there be no significant net fluid transfer across a permeable cell boundary membrane. Thus the invention contrasts sharply with forced flow electrophoresis, electrofiltration and electrodecantation, which require fluid transfer across a boundary membrane, and with free-boundary electrophoresis, in which the absence of a membrane inherently allows liquid transfer. The elimination of liquid transfer across the boundary provides a dual separation and concentration function. This dual function can be illustrated by considering a starting solution, arbitrarily designated A, which contains a mixture of components, such as dissolved or colloidal proteins, to be separated. Under the appropriate conditions for electrophoretic separation, some of the components will migrate across the boundary to a solution on the other side, arbitrarily designated B. Other, differently charged components, e.g., non-migrating species or ions migrating away from the boundary, remain in solution A; they can be considered non-migrating components with respect to the cell boundary. In a forced-flow electrophoretic separation, some of the non-migrating components are carried across the boundary by fluid transport, e.g. from solution A to solution B. This distributes them between solutions A and B, reducing the absolute amount present on both sides of the boundary and diluting the absolute concentration of migrating components obtained in solution B. By way of contrast, in the balanced flow electrophoresis apparatus of the present invention, only the migrating components are moved across the boundary with their resulting concentration and purification in solution B. Simultaneously, the non-migrating components remain in solution A, being purified by separation from the migrating components. Since neither solution is diluted or contaminated by the other, the output streams A and B can both be useful products.

A particularly useful embodiment is the separation of gamma globulin from albumin in solutions such as blood plasma. It has been found that excellent separations can be obtained by subjecting buffered blood plasma directly to balanced flow electrophoresis in the present apparatus. Blood plasma is modified only by buffering to a pH between the isoelectric points of the proteins to be separated (4.7 for albumin and 7.4 for gamma globulin) and employed as one stream, while a compatible buffer solution is employed as the other. A gamma globulin output stream and an albumin output stream can be obtained simultaneously in a one step continuous process, with both products being sufficiently purified to be concentrated, sterilized or otherwise treated by other continuous processes with or without further protein separation steps.

DETAILED DESCRIPTION OF THE INVENTION

Figure 1:
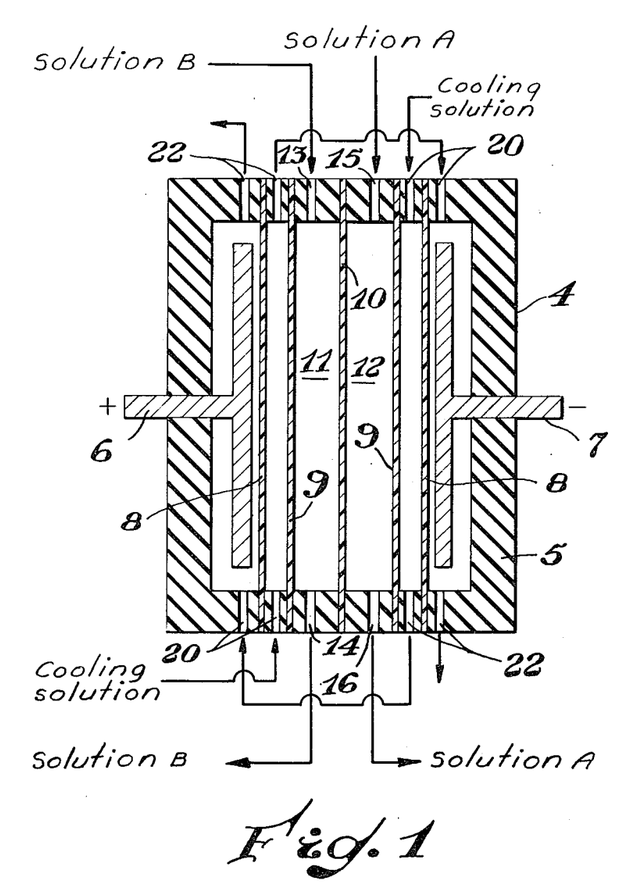
FIG. 1 is a schematic cross-sectional view of one embodiment of the balanced flow electrophoresis cell of the present invention showing the concurrent direction of flow in the various fluid streams.
Figure 2:
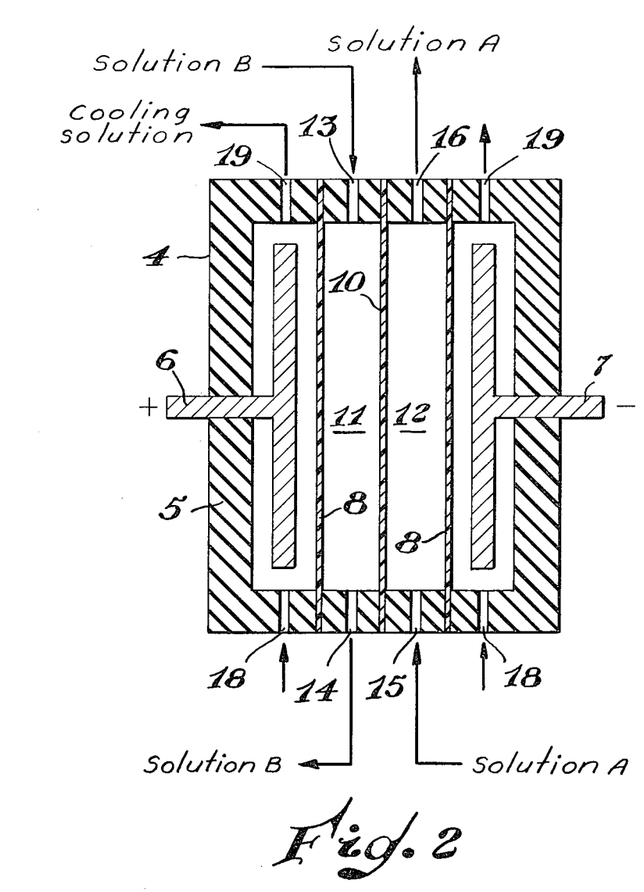
FIG. 2 is a schematic cross-sectional view of another embodiment of the electrophoresis cell of the present invention illustrating a counter flow embodiment.

Referring to FIGS. 1 and 2, the electrophoretic cell stack 4 comprises a cell enclosure 5 which can be made of separate sections of an electrically non-conducting material pressed or clamped together by any suitable retaining means. Disposed within the enclosure 5 are a pair of electrodes, anode 6, and cathode 7. The electrodes 6,7 are mounted in opposite walls of the enclosure 5 and connected by conventional means to a source of direct current for applying the electric field. Also within enclosure 5 there are disposed a plurality of colloid-impermeable membranes 8 extending completely across the interior volume of enclosure 5 and generally parallel to the electrodes 6,7. Membranes 8 are of a semipermeable, non-conducting material such as cellulose acetate membranes or the like used in dialysis, permitting small ions such as inorganic salts, phosphate buffers, citrate buffers, etc. to traverse the membrane while preventing colloidal materials such as blood proteins from passing through the membranes 8. The membranes 8 thus define an inner compartment within enclosure 5. A colloid permeable, non-conducting boundary membrane 10 is disposed within enclosure 5 between membranes 8, dividing the compartment into a pair of cells 11 and 12. Boundary membrane 10 is of a non-conducting material which is permeable to the substance to be separated or concentrated in the apparatus. It may be made of filter paper, filter cloth, ceramic filtering material or the like.

The enclosure 5 includes an inlet 15 to cell 12, and at the opposite end of cell 12, an outlet 16 for passing a fluid stream, e.g. solution A, through cell 12. In a corresponding manner there is provided an inlet 13 to cell 11 and an outlet 14 at the opposite end of cell 11 for passing another stream, e.g. solution B, through cell 11.

In operation, the electric field may result in the formation of undesired concentrations of ionic species, and may also result in formation of gases and heat at the electrodes 6,7. Accordingly, as illustrated in FIG. 2, the electrophoresis stack includes means for introducing a cooling solution, such as a buffer solution into the regions defined by membranes 8 and enclosure 5, e.g. inlets 18 and outlets 19 allow a cooling solution to be introduced into the regions defined by membrane 8 and enclosure 5. To further minimize undesired effects of the electric field, an additional pair of membranes 9, similar to membranes 8, can be disposed in the enclosure 5 between each membrane 8 and the boundary membrane 10, as illustrated in FIG. 1. Appropriate inlets 20, and fluid conduits (illustrated by arrowed lines) and outlets 22 are provided for passing a cooling solution between first one pair of adjacent membranes 8,9 adjacent the anode 6 and then past the cathode 7; and for passing another cooling solution between the pair of adjacent membrane 8,9 which are adjacent the cathode 7, then past the anode 6.

Figure 3:
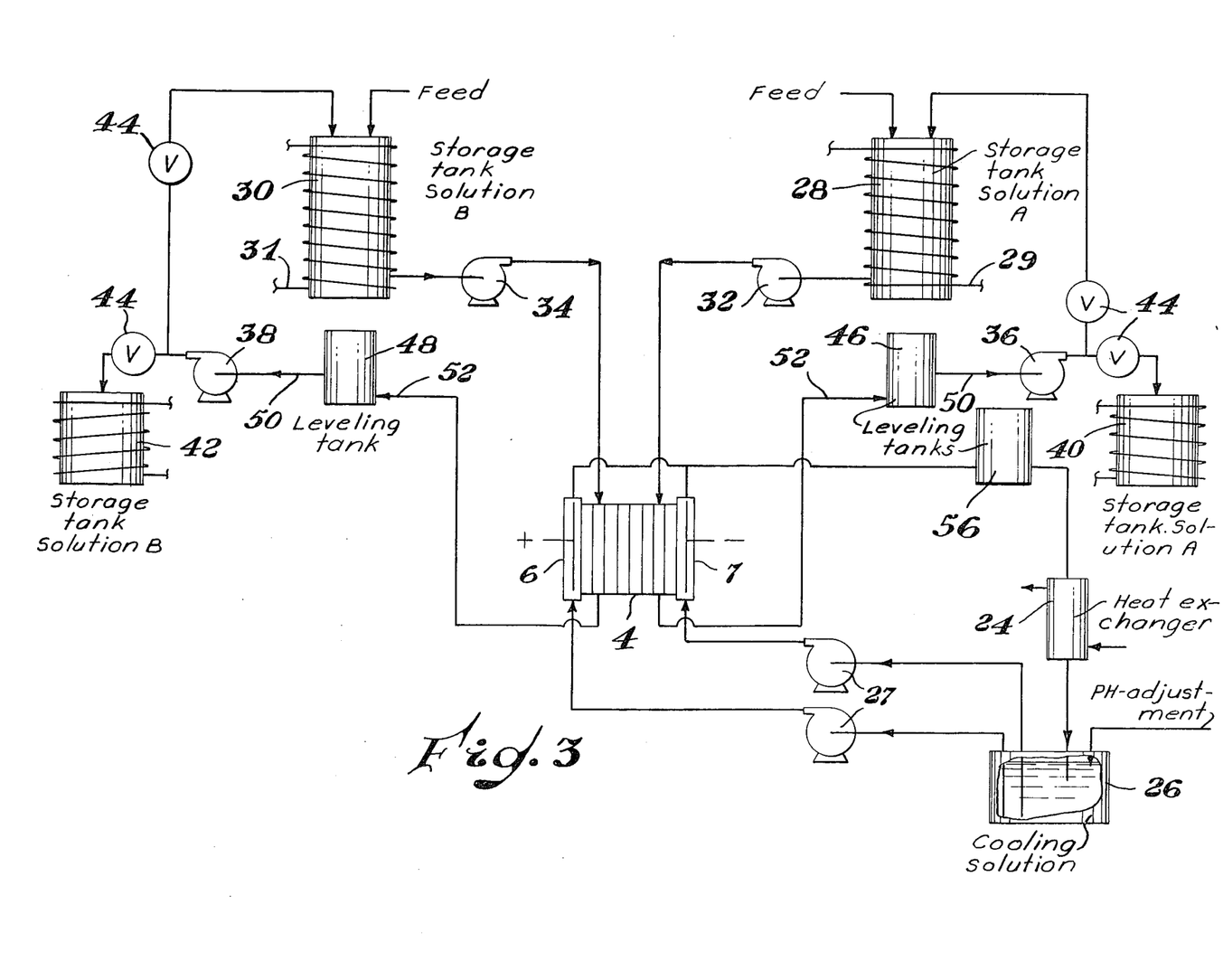
FIG. 3 is a schematic view of the overall apparatus.

The cooling solution streams are preferably recycled to the electrophoretic stack 4, as illustrated in FIG. 3, by passing them through cooling means, e.g., a heat exchanger 24, combining the cooled solutions in a suitable refrigerated vessel, e.g., cooling solution reservoir 26, and dividing the solution and passing it back to the stack 4 by conventional means, e.g. pumps 27. A leveling tank 56 is preferably included in the return line between the stack 4 and reservoir 26. Recombination and mixing of the cooling solution streams outside the cell stack 4 (e.g. in reservoir 26) allows the ionic species formed at the anode 6 and cathode 7 to neutralize each other chemically. Conventional means for adjusting the pH of the cooling solution can be conveniently provided at reservoir 26.

A preferred form of the overall apparatus is illustrated in FIG. 3. The cell stack 4 is not illustrated in detail in FIG. 3. The general features of the cell stack 4 have been described in more detail in reference to FIGS. 1 and 2. If desired, the cell stack 4 can comprise a plurality of cell pairs, each pair having its own permeable boundary membrane 10, and each pair separated from the adjacent cell pairs and from the electrodes by a semipermeable membrane, or preferably by a pair of semipermeable membranes 8,9 to permit a cooling solution to be passed between each cell pair in the stack, as well as between the cell pairs and the electrodes.

As illustrated in FIG. 3, a feed reservoir 28 provided with temperature control means, e.g., cooling coil 29 is provided for a liquid, solution A, to be separated. A similar reservoir 30 with a cooling coil 31 is provided for the other fluid, solution B.

The two solutions, A and B, are introduced into the cell stack 4 at a controlled rate by feed pumps 32, 34; and withdrawn from the stack 4 by a corresponding pair of pumps 36,38. If desired, the processed streams A and B can be divided downstream of pumps 36,38 so that a predetermined portion of each stream is returned to its respective reservoir, 28 or 30, and the remainder of each stream is collected in a corresponding collection reservoir 40,42. The proportion of each solution to be recycled is controlled by conventional means, e.g. valves 44 in the appropriate branches of the fluid circuit. When desired, instead of recycling the streams A and B, their collection reservoirs can serve as feed reservoirs for a second cell stack, or other separatory device.

Intermediate the cell stack 4 and pumps 36,38, the apparatus includes means for balancing the hydrostatic pressure of solutions A and B, e.g., leveling tanks 46,48. In a convenient embodiment, the leveling tanks 46,48 can be simply a pair of vessels each having an inlet 52 and an outlet 50. The inlets 52 are connected to the cell stack 4 on opposite sides of the boundary membrane 10. The outlet 50 of each leveling tank 36,48 are connected to their respective outlet pumps 46,38. In one embodiment, the tanks 46,48 are also overflow tanks, i.e., the outlet 50 on each tank is vertically higher than its inlet 52. The outlets 50 of both tanks are then vertically level with each other to maintain the same hydrostatic pressure head in both solutions A and B. The pressure of the air in both tanks 46,48 above the liquid level is maintained equal by conventional means such as venting both tanks to atmosphere. The leveling tank 50 on the cooling solution line operates in the same manner.

When the leveling tanks 46,48 are arranged as overflow tanks, the apparatus can be operated without the outlet pumps 36,38 if the pumping pressures provided by the feed pumps 32,34 are kept equal, and the cell geometry remains constant. When it is desired to pass the two streams A and B through the device using different pumping pressures or when the cell geometry is subject to change, due to membrane distortion or the like, the outlet pumps 36,38 must be employed. When the outlet pumps 36,38 are in operation, the leveling tanks 46,48 serve only to balance hydrostatis pressure across the boundary membrane 10, and need not serve as overflow tanks. In this mode of operation, the relative height of inlets 52 and outlets 50 is not critical.

In operation, each of the outlet pumps 36,38 is operated at a volumetric flow rate substantially equal to the flow rate provided by its corresponding feed pump 32,34 to ensure that the liquid flow rate does not affect the hydrostatic pressure of solutions A and B in the cell stack 4. Also, the cell stack 4 itself is oriented so that the boundary membrane 10 is substantially vertical (as illustrated by the vertical lines in FIG. 3) to equalize the hydrostatic pressure across the membrane 10.

Operation of the Leveling Tanks and Outlet Pumps

The materials usually employed as semipermeable membranes 8 frequently are subject to severe, distortion in use. Even though the membranes 8 are fastened to the rigid cell support 5 at their edges, the major portion of their surface is exposed in the cell without rigid support, and usually wrinkles or buckles severely when wet. These distortions change the cross-sectional area of the fluid flow path through the cell, resulting in localized erratic variations in liquid pressure as the solution is pumped through the cell.

The boundary membrane 10 is more porous than membranes 8, and is generally of a structurally weaker material such as filter paper or filter cloth. In use the boundary membrane can bulge or sag to one side, decreasing the flow area and increasing the fluid pressure in one stream with a corresponding increase in flow area and reduced pressure on the other side. The internal pressure differences resulting from membrane distortions cause undesirable fluid transport across the boundary membrane 10, resulting in uncontrolled cross-contamination and dilution by mass transport through the boundary. The membrane distortion effects become more severe as the size of the apparatus is increased, with the corresponding decreasing ratio of linear edge support to membrane surface area.

In the apparatus liquid is introduced into and withdrawn from each cell by two pair of pumps, one pair of pumps 32 and 34 upstream and one pair of pumps 36 and 38 downstream of the cell, with both pairs of pumps preferably operating at the same volumetric flow rate. Additionally, a standpipe, or leveling tank 46,48 is provided in the flow paths intermediate the pumps, to provide automatic pressure equalization on both sides of the permeable membrane. The leveling tanks 46,48 are liquid containers each having a liquid inlet and an outlet and having a wall which extends vertically upward above the inlet and outlet to permit containment of a fluid column therein. Each leveling tank 46,48 is thus adapted to function as a standpipe in stabilizing liquid pressure in its respective cell.

In combination with the pumps and with each other, the leveling tanks 46,48 automatically balance the pressures on opposite sides of the boundary membrane 10. The apparatus is constructed so that the liquid level in each leveling tank is above the uppermost portion of the electrophoresis cells, and so that the liquid level in one leveling tank can achieve a pressure-equalizing level relative to the other leveling tank. In most instances, the desired cell geometry and flow rate on opposite sides of the membrane are equal and the liquid levels in the leveling tanks 46,48 will be level with each other under such conditions.

When a pressure difference develops during operation (due to membrane deformation, change in pumping pressure or the like), there is a transient liquid flow through the boundary membrane 10. The apparatus includes means for providing uniform flow rate from the leveling tanks, e.g. downstream outlet pumps 36,38. Thus, any such transient liquid flow across the boundary automatically changes the relative liquid levels in the leveling tanks 46,48 to re-equalize pressure across the boundary membrane 10. In continuous electrophoresis, the automatic pressure compensation provided by the leveling tanks 46,48 and constant flow outlet pumps 36,38 substantially eliminates net liquid flow across the boundary membrane 10.

In practice, the leveling tanks 46,48 can be relatively small; e.g. tubes about 2 centimeters in diameter and 7 to 8 centimeters in height (above their outlets) have given excellent results with cells in which the boundary membrane is about 100 square centimeters in area. In practical separation of blood proteins, the flow rate through each cell is generally low, e.g., 0.25 to 2 milliliters per minute, and the pressure differences across the boundary 10 are also low, generally on the order of one to three millimeters of water, as indicated by observation of the leveling tanks. While the absolute pressure differentials are relatively slight, the resulting fluid flow can be substantial, due to the high porosity and area of the boundary membrane 10.

In large scale operations using a cell stack 4 with a large number of cell pairs, a leveling tank can be economically employed in the output stream from each cell. By using a conventional peristaltic pump, individual constant flow inlet and outlet pumps can be easily employed for large numbers of cells. However, it has been found that the required balanced pressure can be achieved by connecting the outlets of a plurality of cells to a single leveling tank and outlet pump. Further reduction in pumping capacity has been obtained by providing an outlet pump for only one of the two liquid streams, e.g. stream B. In this case the leveling tank on the other stream, e.g. stream A, can function adequately as an overflow tank without requiring a second outlet pump. It will thus be apparent that the invention can be adapted to a wide variety of specific embodiments.

It will be apparent that the flow rates of the two solutions, A and B, can be the same or different, as may be desired, without altering the pressure balance in the stack 4 itself. It will also be apparent that the equal balancing of liquid pressure across the membrane 10 virtually eliminates net fluid transfer across the membrane. Thus mass transport of ions and molecules across the boundary membrane 10 takes place by diffusion and electrophoretic migration only. Since the electrophoretic field strength can readily be made the dominant factor, and since diffusion can be minimized (e.g., by choice of membrane 10, selection of pH and ionic strength of solutions A and B, etc.) the balanced flow electrophoresis system is adaptable to easily controllable precise separations.

In contrast to forced flow electrophoresis, electrodecantation, electrofiltration and the like, balanced flow electrophoresis provides a high degree of control over electrically neutral components, i.e., the components which do not migrate under the influence of the electric field. The invention can thus be employed to separate a mixture of components, giving, as one output stream, a product with a high concentration of the migrating components of one charge and, in a second output stream, a second product enriched in the electrically neutral components and those of opposite charge. Both streams can be used as feed streams for further purification or separation, by balanced flow electrophoresis or other means. Additionally, balanced flow electrophoresis provides higher yields in terms of absolute concentration than the obtainable with forced flow systems.

The following examples illustrate the invention.

EXAMPLE 1

A balanced flow electrophoresis apparatus is assembled using two cell pairs separated from each other and from the electrodes by semipermeable membranes. The anode and cathode employed have cross-sectional areas of 97 square centimeters. The cells have the same cross-sectional area (97 square centimeters) and each chamber in each cell is 0.18 centimeters thick. Filter paper is employed as the boundary membrane. The apparatus is employed to separate albumin from gamma globulin in human blood plasma. Clear plastic leveling tanks are employed in the outlet lines, and a multiple-channel peristaltic pump is used to provide constant flow pumping in the inlet and outlet lines. During several different runs, the net fluid flow in both streams has been measured by collecting the output streams over uniform time intervals such as five or ten minutes. These observations indicated that the fluid flow rates in both streams were substantially equal (less than about 5 percent difference). In most cases, no differences would be detected by volumetric measurement in graduated cylinders.

In one such operation, filtered, undialyzed human plasma, buffered to a pH of 6.4 with 0.025 molar phosphate buffer U.S.P. is employed as the A stream. The B stream is aqueous 0.025 molar phosphate buffer, pH about 6.35. The cell stack is primed with about 50 milliliters of the same buffer, and the A and B streams are passed through the cell stack at a flow rate of 1.0 milliliter per minute, the A stream flowing upward and the B stream flowing downward. The electrodes are connected to a direct current power supply to pass a constant current of one ampere at 32-24 volts (the voltage decreasing during the separation) through the cell stack. The input temperatures of the A and B streams are about 4° C. at the reservoirs and the output temperatures between 19° C. and 22° C.

The streams are analyzed for total protein by the biuret reaction. Specific protein contents are assayed by cellulose acetate electrophoresis. The plasma feed stream A has an initial protein content of 4.03 grams per liter, of which 64.9 percent, 2.62 gm/l, is albumin. The output stream A is reduced in total protein to 0.90 gm/l so that absolute albumin content is 0.45 gm/l (50.0 percent). The output buffer stream B is enriched in protein to an absolute concentration of 2.80 grams per liter of which 2 gm/l, 71.4 percent is albumin. (Results uncorrected for dilution effect of priming buffer.)

EXAMPLE 2

In another operation the A stream is a mixture of 63.9 percent human albumin and 36.1 percent gamma globulin in aqueous 0.025 M phosphate buffer, pH 6.38, total protein concentration 1.73 gm/liter (1.11 gm/liter albumin and 0.62 gm/liter gamma globulin). The B stream is aqueous 0.025 molar phosphate buffer, pH 6.4. Both streams are primed initially with 50 milliliters of the same buffer before the protein mixture is introduced. The A stream is fed downward and the B stream upward at one milliliter per minute, and the current employed is 1.0 ampere at 26 volts. The total output of the A stream is collected, assayed and found to contain 0.34 grams per liter total protein, substantially all gamma globulin. Allowing for dilution with the priming buffer, this represents a yield of 100 percent gamma globulin in a concentration of 0.41 grams per liter of starting protein solution, with an increase in the purity of the gamma globulin from 36.1 percent to 100 percent.

300 Milliliters of the B stream are found to contain 1.08 gm/liter total protein, of which 0.93 gm/liter or 86.3 percent is albumin and 0.15 gm/liter or 13.7 percent. is gamma globulin. This represents a substantially complete transfer of the albumin from the A to the B stream, with an increase in purity of albumin from 63.9 percent to 86.3 percent of the protein content.

In a preferred form of operation, both streams, A and B, are fed concurrently downward through the cell stack, as depicted in FIGS. 1 and 3. The following example utilizes apparatus similar to that of Examples 1 and 3, with two cell pairs, in a downward concurrent flow separation of blood plasma.

EXAMPLE 3

Blood plasma adjusted to pH 6.35 with a $Na_2HPO_4$, $NaH_2PO_4$, $H_3PO_4$ buffer is fed as the A stream at a rate of 0.5 milliliters per minute. This stream contains albumin and alpha, beta and gamma globulins in ratios of 59.5, 13.9, 11.4 and 15.2 percent, initially. The B stream employed is 0.025 Molar phosphate buffer U.S.P., pH 6.35, fed downward at 0.5 ml/min. The current employed is 1.2 ampere at 37 volts. The protein composition of the exit B stream is found to be 84.6 percent albumin and 6.2, 6.2 and 3.0 percent alpha, beta and gamma globulins.

In a second run at a flow rate of 1.0 ml/min, with 1.00 ampere at 34 volts, protein composition of the starting plasma stream is 67.1, 9.4, 9.4 and 14.1 percent albumin, and alpha, beta and gamma globulins, respectively. The exit B stream is found to contain no gamma globulin, and 91 percent albumin, the remaining 9 percent being alpha and beta globulins.

In operations such as those described above, protein precipitation (generally fibrinogen) takes place outside the cell on the holding of the output A stream. No significant fibrinogen precipitation or membrane fouling is detected in the cell stack 4 itself.

The invention can also be applied to the supernatant liquids from plasma protein fractionation methods based upon alcohol precipitation. (See, for example, Cohn et al., U.S. Pat. Nos. 2,390,074 and 2,469,193, and J. Am. Chem. Soc. 68, 469 (1946); Gerlough, U.S. Pat. No. 2,710,293 and 2,710,294; and Hink, U.S. Pat. No. 2,958,628.) In such use, the alcoholic supernatant can be fed directly to the balanced flow electrophoresis cell stack 4 after adjustment of pH to between the isoelectric points of the plasma proteins to be separated. During electrophoresis, the alcohol can be dialyzed out of the A and B streams into the cooling solution, if desired, by appropriate choice of colloid-impermeable membranes 9 and relative flow rate.

In a particularly useful embodiment, the balanced flow electrophoresis is employed in conjunction with electrodialysis to purify blood proteins. It has been found that electrodialysis of the albumin enriched B stream results in selective precipitation of globulins therein, thus improving purification of the albumin. In general, this process can be carried out by subjecting plasma (as the A stream) to balanced flow electrophoresis to separate albumin into the buffered B stream, and then passing the B stream through a conventional electrodialysis cell having conventional ion exchange membranes, and separating the resulting liquid from the resulting precipitate.

EXAMPLE 4

In a representative operation, undialyzed, buffered human blood plasma, pH of 6.38–6.45, 0.02–0.03 molar phosphate buffer U.S.P. (United States Pharmacopoeia) is introduced as the A stream into a balanced flow electrophoresis stack, using similar 0.025 molar buffer as the B stream. Electrophoresis is carried out using concurrent downward flow at a rate of one milliliter per minute on both streams, and a direct current field of 2.2 amperes at 56 volts. Analysis of an aliquot from the output B stream indicates a total protein content of 25.2 grams per liter, of which 78 percent is albumin.

The B stream is pumped through an electrodialysis cell comprising an anode compartment with a ruthenium oxide coated titanium electrode, an anion exchange resin membrane (commercially available from Ionics) a center compartment for the B stream protein solution, a cation exchange resin membrane (Ionics) and a cathode compartment with a nickel cathode. Electrode and ion exchange membrane areas are 97 square centimeters. Refrigerated aqueous 0.1 molar solution of sodium sulfate and 0.1 molar sodium thiosulfate is pumped through the electrode compartments as a cooling sweep stream. The B stream is circulated through the cell at 400 milliliters per minute while a direct current electric field of 5 volts is applied between the electrodes. The initial current is 0.73 amperes, dropping to 0.02 amperes, by the end of the run. The sweep stream temperatures if 5°–6° C., and the B stream temperatures 7°–9° C.

The output stream is centrifuged and the supernatant liquid is found to contain 21.4 grams total protein per liter, 86.5 percent albumin.

In a similar operation, a B stream containing 7.9 grams per liter total protein, 88 percent albumin, is similarly subjected to electrodialysis. The precipitate which forms during the run is separated by centrifugation. The supernatant solution is analyzed, and found to contain 6.5 grams total protein, of which 91.6 percent is albumin.

EXAMPLE 5

In another useful embodiment, the protein solution to be separated is subjected to multiple balanced flow electrophoretic separations.

In apparatus similar to that described in Examples 1–3, filtered, undialyzed human blood plasma was buffered to pH 6.4 with phosphate buffer. Aliquots were taken for analysis, and 235 milliliters of the buffered, filtered plasma were used as the A stream. 0.025 Molar, pH 6.4 phosphate buffer was used as the B stream. The streams were fed to the electrophoresis cell at 0.5 ml/minute, concurrently downward, using a direct current of 1.0 ampere. The electrophoresis cell was cooled to provide temperatures at the inlets and outlets of about 14° C. and about 16° C. The output stream B was reserved.

The output of stream A was collected and an aliquot was buffered again to pH 6.4, filtered, and used as the A feed stream with fresh 0.025 molar, pH 6.37 phosphate buffer as the B stream, under similar electrophoresis contitions. Both the A and B streams were collected.

The analyses of the original A feed stream, and the A and B output streams from the first and second passes (A, B and A', B', respectively) are set out below in grams per liter.

| | Feed | Outputs | | | |
|---|---|---|---|---|---|
| | A | A | A' | B | B' |
| Total protein | 48.0 | 24.0 | 11.20 | 24.8 | 10.5 |
| Gamma-Globulin | 6.82 | 4.8 | 3.56 | 0.99 | 0.15 |
| Beta-Globulin | 4.70 | 2.14 | .82 | 1.49 | 0.37 |
| Alpha-globulin | 6.24 | 2.14 | .72 | 2.48 | 1.11 |
| Albumin | 30.24 | 14.93 | 6.10 | 19.84 | 8.87 |

In terms of percentage of total protein, the albumin content was 63 percent in the original A feed, 80.0 percent in the first B output and 84.5 percent in the second B' output, with corresponding reductions of gamma globulin in the same streams from 14.2, to 4.0 to 1.4 percent. Gamma globulin was purified in the A streams, from 14.2 percent of total proteins in the feed, to 20.0 percent in the first A output, to 31.8 percent in the second, A' output.

The original A feed stream represents about 7.11 grams albumin in the starting feed stream. On a gross basis (ignoring amounts lost in the apparatus at the ends of runs and amounts not collected during priming) 209 ml. of the first B stream and 185 ml. of the second B' stream were collected. Thus on a gross basis, 5.79 grams, or about 81.5 percent of the albumin in the feed, was recovered in the B streams.

What is claimed is:

1. An apparatus for continuous electrophoresis comprising
  an electrophoresis cell defined by a pair of membranes;

a permeable boundary membane in the cell generally parallel to the membranes and dividing the cell into the first and second separate compartments on opposite sides thereof;

separate inlet means on the cell for continuously feeding a separate solution into each compartment;

separate outlet means at a location spaced from the inlet means on the cell for separately withdrawing each solution from its compartment continuously;

means for passing a direct current through the cell and across the boundary membrane and compartments; and balancing means associated with the inlets and outlets for continuously maintaining the fluid pressure in the first compartment substantially equal to the fluid pressure in the second compartment.

2. Apparatus of claim 1 further comprising first and second inlet pump means connected to a corresponding inlet means;

a first outlet pump means connected to the corresponding outlet means, said first outlet pump means being adapted to operate at a volumetric flow rate substantially equal to the first inlet pump means;

a first leveling tank means connected in the resulting fluid path between the first inlet pump means and the outlet pump means and situated higher than the cell for providing a hydrostatic pressure head, and second leveling tank means connected in the fluid path which comprises the second inlet and outlet means and situated in a pressure balancing relation to the first leveling tank and the cell.

3. Apparatus of claim 2 wherein the boundary membrane is oriented in a vertical plane and wherein the second leveling tank means is situated higher than the cell and level with the first leveling tank.

4. Apparatus of claim 3 wherein the inlet means on the cell are situated on an upper end thereof, and the outlet means are situated on a lower end thereof thereby providing for concurrent downward fluid flow through the cell; and wherein each leveling tank means is connected between an outlet means and the corresponding outlet pump.

5. Apparatus of claim 2 further comprising a second outlet pump means connected downstream of the second leveling tank means, and adapted to operate at a volumetric flow rate substantially equal to that of the second inlet pump means.

* * * * *

UNITED STATES PATENT AND TRADEMARK OFFICE
CERTIFICATE OF CORRECTION

PATENT NO. : 4,043,895
DATED : August 23, 1977
INVENTOR(S) : Gerhard Gritzner

It is certified that error appears in the above-identified patent and that said Letters Patent are hereby corrected as shown below:

Column 2, line 48, insert quotation marks before and after capital "A".

Column 2, line 54, insert quotation marks before and after capital "B".

Column 5, line 10, delete "36" and insert --46--.

Column 5, line 11, delete "46" and insert --36--.

Column 7, line 36, delete "the" and insert --are--.

Column 8, line 43, Example 2, delete the period after cent.

Column 10, line 33, Example 5, delete "conitions" and insert --conditions--.

Column 10, line 44, Example 5, delete "globulin" and insert --Globulin--.

UNITED STATES PATENT AND TRADEMARK OFFICE
CERTIFICATE OF CORRECTION

PATENT NO. : 4,043,895
DATED : August 23, 1977
INVENTOR(S) : Gerhard Gritzner

Page 2 of 2

It is certified that error appears in the above-identified patent and that said Letters Patent are hereby corrected as shown below:

Column 11, Claim 1, line 3, delete "the" in front of first and second separate.

Signed and Sealed this

Tenth Day of January 1978

[SEAL]

Attest:

RUTH C. MASON
Attesting Officer

LUTRELLE F. PARKER
Acting Commissioner of Patents and Trademarks